United States Patent [19]

Nüsslein et al.

[11] 4,112,107
[45] Sep. 5, 1978

[54] 5-NITROTHIAZOLE CONTAINING PESTICIDE COMPOSITION

[75] Inventors: Ludwig Nüsslein; Ernst Albrecht Pieroh, both of Berlin, Fed. Rep. of Germany

[73] Assignee: Schering Aktiengesellschaft, Berlin & Bergkamen, Fed. Rep. of Germany

[21] Appl. No.: 840,006

[22] Filed: Oct. 6, 1977

[30] Foreign Application Priority Data

Oct. 8, 1976 [DE] Fed. Rep. of Germany ....... 2646044

[51] Int. Cl.² .......................... A01N 9/12; A01N 9/20
[52] U.S. Cl. .................................................. 424/270
[58] Field of Search ........................................ 424/270

[56] References Cited

U.S. PATENT DOCUMENTS

| 3,839,572 | 10/1974 | Verge et al. | 424/270 |
| 3,850,939 | 11/1974 | Elslager et al. | 424/270 |
| 3,907,819 | 9/1975 | Herkes | 424/270 |

OTHER PUBLICATIONS

Chemical Abstracts, vol. 74, (1971), p. 31748g.

*Primary Examiner*—V. D. Turner
*Attorney, Agent, or Firm*—Michael J. Striker

[57] ABSTRACT

A pesticide which contains at least one compound of the formula

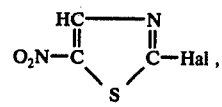

in which Hal is halogen. The compositions have both a fungicidal and nematicidal action and have a high compatibility with agriculturally and horticulturally useful plants.

6 Claims, No Drawings

5-NITROTHIAZOLE CONTAINING PESTICIDE COMPOSITION

BACKGROUND OF THE INVENTION

Pesticides which have both a fungicidal and a nematicidal action are known. Among the compounds of this kind which are in use are compositions in which the active agent is tetrahydro-3,5-dimethyl-2H-1,3,5-thiadiazin-2-thione (known under the name "Dazomet") and N-(tri-chloromethyl-thio)-cyclohex-4-ene-1,2-dicarboximide (known under the name "Captan").

The shortcoming of these pesticidal agents is that they either do not have sufficient plant compatibility or are not effective against nematodes.

It is an object of the present invention therefore to provide for an agent which is effective both against fungi and against nematodes and at the same time has a high plant compatibility.

SUMMARY OF THE INVENTION

This object is met by a composition which is characterized by a content of at least one compound of the formula

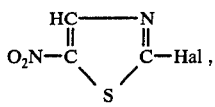

in which Hal is halogen.

Among the compositions of the invention those in which Hal is chlorine or bromine have a particularly distinct fungicidal and nematicidal action.

Surprisingly, the compounds of the invention are not phytotoxic when used in reasonable amounts and they therefore do not negatively affect the plant growth. Due to these properties they can be used for general application to the ground both in agricultural and in horticultural establishments. Because of their broad spectrum of activity they make it unnecessary to use separate agents for different organisms as frequently occur together in the same area.

Among the phytopathogenic nematodes against which the compounds of the invention can be used there are, for instance, the genera of the wandering root knot nematodes such as Tylenchlorhynchus, Pratylenchus, Paratylenchus, Helicotylenchus, Xiphinema, Trichodorus and Longidorus and root gall nematodes, as for instance *Meloidogyne incognita, M. arenaria, M. hapla;* cyst forming root namatodes, as e.g. *Heterodera rostochiensis, Heterodera schachtii* and others.

The compounds of the invention can also be used against phytopathogenic fungi in the ground such as *Pythium ultimum, Pythium irregulare, Pythium silvaticum, Pythium splendens, Pythium aphanidermatum, Phytophthora fragariae, Rhizoctonia solani, Thielaviopsis basicola, Fusarium solani, Fusarium avenaceum* and others.

The fungicidal action is effective in addition against microorganisms occurring in plant parts above ground such as *Botrytis cinereamus, Piricularia oryzae,* and seed attacking microorganisms, e.g. *Tilletia caries, Pseudomonas phaseolicola* and is comparatively more effective than the prior art agents having similar applications.

It has also been found that the compounds of the invention have a high insecticidal and acaricidal activity particularly in the vaporous or gas phase so that they can be used also against insects in the ground.

The compounds of the invention have furthermore a bactericidal action which permits to use them against all kinds of pests, particularly phytopathogenic pests.

DETAILS OF THE INVENTION AND PREFERRED EMBODIMENTS

The compositions can be applied either with one agent of the invention by itself, or with a mixture of at least two of these agents. If desired, other fungicidal, nematicidal, herbicidal or other pesticidal agents may be added according to the specific purpose.

The compounds are preferably used in the form of compositions such as powders, dusting compositions, granulates, solutions, emulsions or suspensions, upon addition of liquid and/or solid carrier materials or diluents. If desired, auxiliary agents may be added such as wetting agents, adhesion promoting agents, emulsufiers and/or dispersion agents.

Suitable liquid carrier materials are water, mineral oils or other organic solvents such as xylene, chlorobenzene, cyclohexanone, dioxane, acetonitrile, acetic acid ester, dimethylformamide, isophorone and dimethylsulfoxide.

Solid carrier materials are for instance lime, kaolin, chalk, talc, attaclay and other clays as well as natural or synthetic silicic acid.

In the compositions there may be added surface active agents of which, for instance, the following may be mentioned: salts of the lignosulfonic acids, salts of alkylated benzosulfonic acids, sulfonated acid amides and their salts, polyethoxylated amines and alcohols.

Where the compositions are to be used for the purpose of seed disinfection (seed steep) dyestuffs may also be added in order to give the treated seed goods a distinct color.

The amount of the active agent or agents can be varied widely. The exact concentration depends mainly on the amounts in which the compositions are to be used in treating the ground. The compositions may, for instance, include about 1 to 80% by weight, preferably between 20 and 50% by weight of active agents, and about 99 to 20% by weight of liquid or carrier materials. There may also be added 20% by weight of surface active agents upon corresponding reduction of the carrier materials.

The compounds used in the present invention are known as such and can be made by processes known in the prior art.

As specific examples of the compounds there may be named the following: 2-chloro-5-nitrothiazole, 2-bromo-5-nitrothiazole and 2-iodo-5-nitrothiazole.

The making of the compositions of the invention can likewise be carried out by conventional methods, for instance by mixing or dissolving the active agent or agents with or in the carrier materials or means of application. If necessary, mixing devices may be used in the mixing process.

The amount to be used depends largely also on the type of preparation, on the type of application, on the desired purposes of the application and the type of pests which are involved in the application.

The following examples will further illustrate the types of application and the results obtained therewith.

EXAMPLE 1

Tests showing the concentration limits involving rootgall nematodes (Meloidogyne sp.)

A 20% pulverulent composition was mixed in uniform manner in the earth which had been heavily contaminated by rootgall nematodes. The treated earth was then filled into earthen vessels of a capacity of 0.5 liters earth and 10 grain of cucumber seeds of the type "Guntruud" were exposed to the action of the treated ground.

A culture time of 28 days in a hothouse at a temperature of 24° to 26° C. then followed. The cucumber roots were then washed out and were examined in a water bath regarding the incidence of nematodes. The reduction of the incidence due to the active agents of the invention was calculated in percentages.

Effective agents, amounts applied and reduction of incidence appear from the following Table I.

TABLE I

| Compound | Active agent concentration in mg per liter of earth | Reduction of infestation without a waiting period | Reduction of infestation with 3 days waiting period prior to seed |
|---|---|---|---|
| 2-chloro-5-nitrothiazole | 20 mg | 99% | 100% |
| 2-bromo-5-nitrothiazole | 20 mg | 98% | 99% |
| Comparison compound | | | |
| Dazomet | 20 mg | — | 93% |

EXAMPLE 2

Test of plant compatibility carried out with cress (Lepidium sativum)

The active agents were admixed in uniform manner with the earth and the earth was then filled in earthen vessels of a capacity of 1 liters of earth so as to form an earth column of 10 to 11 cm. Without a waiting period there was then effected the seeding of 2 g of cress seeds per vessel and the seed was then covered with sterile quartz sand. The harvesting of the cress was effected after a growth period of 7 days at 22° to 24° C. in order to determine the weight of the fresh plants.

Active agents, amounts applied and results appear from the following Table II.

TABLE II

| Compound | concentration of active agent in mg per liter of earth | weight of the fresh plant obtained in dampened compost earth from 2 g seed | weight of the fresh plants obtained in non-dampened compost earth from 2 g seed |
|---|---|---|---|
| 2-chloro-5-nitrothiazole | 40 mg | 25 g | 26 g |
| 2-bromo-5-nitrothiazole | 40 mg | 26 g | 18 g |
| Comparison compound | | | |
| "Dazomet" | 40 mg | 14 g | 0 g |
| Untreated ground | | 24 g | 0 g |

EXAMPLE 3

Test with *Pythium ultimum*

A 20% pulverulent composition according to the invention was mixed in uniform manner with the earth which had been heavily infested with *Pythium ultimum*. The treated earth was then filled in earthen vessels of a capacity of 1 liter earth. Thereupon, and without a waiting time, 25 grain of garden peas of the type "Wunder von Kelvedon" (miracle of Kelvedon) were then seeded into each vessel. After a growth time of 3 weeks at 20° to 24° C. the number of healthy peas was determined and an evaluation of the soundness of the roots was carried out on a scale from 1 to 4.

Active agents, amounts of application and results appear from the subsequent Table III.

TABLE III

| Compounds | Concentration of active agent in mg/liter of earth | Number of sound peas | Evaluation of roots (scale from 1-4) |
|---|---|---|---|
| 2-chloro-5-nitrothiazole | 20 mg | 22 | 4 |
| | 30 mg | 24 | 4 |
| | 40 mg | 24 | 4 |
| | 50 mg | 25 | 4 |
| | 100 mg | 25 | 4 |
| 2-bromo-5-nitrothiazole | 20 mg | 22 | 3 |
| | 30 mg | 23 | 4 |
| | 40 mg | 25 | 4 |
| | 50 mg | 23 | 4 |
| | 100 mg | 25 | 4 |
| Comparison compound | | | |
| "Captan" | 50 mg | 7 | 1 |
| | 100 mg | 8 | 1 |
| Dampened ground | | 25 | 4 |
| Untreated ground | | 0 | 1 |

The root evaluation scale is based on the following findings:

4 = white roots without fungus necrosis
3 = white roots with minor fungus necrosis
2 = brown roots, already somewhat stronger fungus necrosis
1 = strong fungus necrosis, roots rotten.

EXAMPLE 4

Activity against pythium-caused soft rot and root rot in a culture of tulips sprouting at 5° C.

At first the ground was treated with a 20% pulverulent composition of the invention based on 2-bromo-5-nitrothiazole. There were then planted in the ground peeled tulip bulbs of the type "Kees Nelis".

The composition of the invention had been admixed to the ground in a uniform manner to a depth of 12 cm. There was a natural infestation with Pythium sp.

After a growth time of 38 days at increasing temperatures from 13° to 18° C. the flowers were cut.

The amounts applied, the plant loss and the fresh weight of plants appear from the following Table IV.

TABLE IV

| Compound | gram of active agent per m² | total loss of plants | average weight of the fresh tulip plants ready to be cut | average weight of the fresh plants in percentage relative to the control in dampened ground |
|---|---|---|---|---|
| 2-bromo-5-nitrothiazole | 2.5 g | 0% | 35 g | 117% |
| | 5.0 g | 0% | 34 g | 113% |
| | 10.0 g | 0% | 31 g | 103% |
| dampened ground | — | 0% | 30 g | 100% |
| infested ground | — | 53% | 22 g | 73% |

EXAMPLE 5

Fungicidal activity in an enclosed space

The active agent was applied by dripping in the form of a suspension onto strips of cellulose which were placed in glasses as used for canning of a capacity of 1 liter. In each glass there were placed two open Petri dishes inoculated with a test fungus. The glasses were then loosely covered with a lid.

After an action period period of 48 hours at 20° C. the fungus dishes were removed, closed with a neutral lid and stored at room temperature. After another 14 days the fungus growth was evaluated.

In the following table the limit values of applied compound are stated at which no fungus growth was observed.

TABLE V

| Limit values after application of 2-bromo-5-nitrothiazole | |
|---|---|
| Test fungus | Amount of compound per liter of air space |
| Botrytis cinerea | 1 mg |
| Rhizoctonia solani | 1 mg |
| Phoma betae | 1 mg |
| Fusarium avenaceum | 2 mg |
| Phytophthora cryptogea | 2 mg |
| Phytophthora nicotianae | 2 mg |
| Pythium splendens | 4 mg |

EXAMPLE 6

Insecticidal action in an enclosed space

The compounds were applied in the form of aqueous suspensions. Cellulose pads which had been steeped in 10 ml of a broth of the inventive composition involving the agent below indicated in Table VI were placed in air-tight closed stand-up glass vessels of 7 liter capacity. The test animals or test stages had previously been introduced into the glass vessels in small cages which were accessible only to the vaporous phase of the active agent.

In this manner there were tested per concentration the following:

(A) 25 adult houseflies (*Musca domestica*)
(B) 20 adult specimens of the grain weevil (*Sitophilus granarius*)
(C) 5 LIII of the Mexican bean beetle (*Epilachna varivestis*)
(D) 10 larvae (10–12 days old) of the German cockroach (*Blattella germanica*)
(E) a potted broad bean plant (*Vicia faba*) which had been heavily infested with wingless stages of the black bean leaf louse (*Aphis fabae*)
(F) 10 adult females of the stringbean mite (*Tetranychus urticae*) placed on a leaf fragment of the bushbean (*Phaseolus vulgaris*)
(G) 10 LIII of the cabbage cockroach (*Plutella maculipennis*)
(H) 10 LII of the cotton owl (*Spodoptera littoralis*)
(I) 1 egg sac of the cotton owl (*Spodoptera littoralis*)

The following table shows the concentration of active agents in g per cubic meter of air space and the activity in percent.

TABLE VI

| Compound | Concentration of active agent in g/m$^3$ | Lethal action on the test organisms expressed in percentages of the total amounts of organisms | | | | | | | | |
|---|---|---|---|---|---|---|---|---|---|---|
| | | A | B | C | D | E | F | G | H | I |
| 2-bromo-5-nitro-thiazole | 8 | 100 | 100 | 100 | 100 | 100 | 100 | 100 | 100 | 100 |
| | 4 | 100 | 98 | 100 | 100 | 100 | 100 | 100 | 65 | 100 |
| | 2 | 93 | 87 | 100 | 100 | 100 | 100 | 60 | 55 | 100 |

EXAMPLE 7

Test with larvae of the black meal worm (*Tenebrio molitor*)

The compositions of the invention were used in the form of aqueous suspensions. Ten adolescent larvae, each, of the black meal worm (*Tenebrio molitor*) were then exposed to a prepared substrate for a duration of 7 days. The lethal effects were then determined in percentages.

The following Table 7 shows the lethal action and the amount of active agent concentration in percentages. The substrate consisted of 2 ml each of the suspension applied to 50 cm$^3$ of a mixture of sand and earth in synthetic Petri dishes.

TABLE VII

| Compound | Concentration of active agent in percentages of substrate | Mortality in percentages |
|---|---|---|
| 2-chloro-5-nitrothiazole | 0.2 | 100 |
| 2-bromo-5-nitrothiazole | 0.2 | 100 |
| | 0.1 | 85 |

EXAMPLE 8

Test with maggots of the housefly (*Musca domestica*)

The compositions of the invention were applied as aqueous suspensions. 10 ml of a broth of the inventive composition were applied by eyedropper to 5 g of sawdust in Petri dishes of glass. After impregnating the medium with the broth twenty 5-day old maggots of the housefly were placed in each of the dishes. The dishes were closed and left for 48 hours in the dark. Thereafter the lethal effect was determined in percentages.

The following Table VIII shows the lethal effect and the concentration of active agent of the composition of the invention expressed in percentages:

TABLE VIII

| Compounds | Concentration of active agent in percentages of substrate | Mortality in percentages |
|---|---|---|
| 2-chloro-5-nitrothiazole | 0.1 | 100 |
| 2-bromo-5-nitrothiazole | 0.1 | 100 |

EXAMPLE 9

Test with Piricularia oryzae

*Piricularia oryzae*, the fungus cause of a disease of the rice, was sprayed as a suspension of conidia onto rice seedlings which had previously been sprayed so as to be dripping wet with the compounds indicated in the table. The leaf spots were counted after 5 days and the action was then calculated relative to the untreated control.

TABLE IX

| Compound | Percent of active agent relative to seedlings | Percent of activity |
| --- | --- | --- |
| 2-chloro-5-nitro-thiazole | 0.3 | 77 |
| Comparison compound | | |
| 2-(4-amino-2-pyrimidonyl)-5-(3-amino-5-N$^1$-methyl-guanidinovaleroyl-amino)-3,4-dehydroxane-2-carboxylic acid | 0.3 | 70 |
| Untreated | —.— | 0 |

Phytotoxity was not observed.

EXAMPLE 10

Test with Botrytis cinerea

Petri dishes with an agar nutrient containing the compounds of the invention indicated in the table were inoculated with the mycelium of an agar culture of the fungus *Botrytis cinerea* which is the cause of the gray mold. After 5 days incubation at 25° C. the increments of mycelium were measured.

TABLE X

| Compounds | Concentration of active agent (ppm) relative to culture | Inhibition of growth expressed in percentages |
| --- | --- | --- |
| 2-chloro-5-nitro-thiazole | 30 | 100 |
| | 10 | 100 |
| 2-bromo-5-nitro-thiazole | 30 | 100 |
| | 10 | 100 |
| Comparison compound | | |
| N-trichloromethylthio-phthalimide | 30 | 79 |
| Untreated | 0 | 0 |

EXAMPLE 11

Test with Pseudomonas phaseolicola

*Pseudomonas phaseolicola*, the bacterial cause of the seed-transferred grease spot illness of the beans, were placed in a suspension and were spread, as conventional, by eyedropper inoculation on a nutriment medium. In addition 20 mg of active agent were placed in a dish in a manner that the material to be tested remained without direct contact with the active agent which latter could be effective on the organism only through the vapor phase. Evaluation was effected after 2 days:

TABLE XI

| Compound | % Activity |
| --- | --- |
| 2-bromo-5-nitrothiazole | 100 |
| Comparison compound | |
| Tetramethylthiuramidsulfide | 7 |

TABLE XI-continued

| | |
| --- | --- |
| Untreated | 0 |

EXAMPLE 12

Test with Tilletia caries

Wheat grains were infested with Tilletia caries, the fungus cause of a seed transferred disease of the wheat. The dosage was 3 g of fungus spores per kg of wheat grains. The wheat grains were then treated with the compositions of the invention indicated in the table below. They were thereupon placed in moist loam and incubated at 11° C. They were removed after 5 days. The spores remaining in the loam were incubated for another 5 days at 11° C. and the percentage spore germination was then determined.

TABLE XII

| Compound | mg of active agent per 100 g of seed | inhibition of germination of the spores in % |
| --- | --- | --- |
| 2-chloro-5-nitro-thiazole | 50 | 99.8 |
| 2-bromo-5-nitro-thiazole | 50 | 100 |
| Untreated | 0 | 0 |

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A method of protecting plants against phytopathogenic earth fungi, nematodes, insects and acarides, the said method comprising applying to the plants or to the ground in which the plants are growing a composition comprising from 1 to 80% by weight of at least one compound of the formula

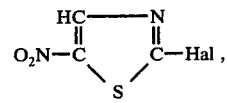

wherein Hal is halogen and 99 to 20% by weight of a liquid or solid carrier material.

2. The method of claim 1 wherein Hal in said formula is chlorine.

3. The method of claim 1 wherein Hal in said formula is bromine.

4. The method of claim 1 wherein the compound of said formula is present in amounts from 20 to 50%.

5. The method of claim 1 in which the said compound is selected from the group consisting of 2-chloro-5-nitrothiazole, 2-bromo-5-nitrothiazole and 2-iodo-5-nitrothiazole.

6. The method of claim 1 in which the said composition additionally includes up to 20% by weight of a surface active agent in which case the amount of said solid or liquid carrier material is correspondingly reduced.

* * * * *